(12) United States Patent
Morinaga et al.

(10) Patent No.: US 7,335,675 B2
(45) Date of Patent: Feb. 26, 2008

(54) AQUEOUS SUSPENSION FORMULATION FOR FOLIAR APPLICATION FUNGICIDE

(75) Inventors: Koichi Morinaga, Mobara (JP); Yuji Yanase, Mobara (JP); Kanemitsu Miyama, Mobara (JP); Hideo Kawashima, Mobara (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/564,851

(22) PCT Filed: Jul. 7, 2004

(86) PCT No.: PCT/JP2004/009986

§ 371 (c)(1), (2), (4) Date: Jan. 17, 2006

(87) PCT Pub. No.: WO2005/006863

PCT Pub. Date: Jan. 27, 2005

(65) Prior Publication Data

US 2006/0235066 A1    Oct. 19, 2006

(30) Foreign Application Priority Data

Jul. 18, 2003    (JP)    ............... 2003-199289

(51) Int. Cl.
*A01N 43/56* (2006.01)
*A01N 25/04* (2006.01)
*A01N 25/30* (2006.01)

(52) U.S. Cl. ............. 514/406; 514/762; 514/765; 514/772.1; 514/772.3; 514/782; 514/785; 514/789; 424/407

(58) Field of Classification Search ............. 574/406, 574/772.1, 782, 789
See application file for complete search history.

(56) References Cited

U.S. PATENT DOCUMENTS 5,747,518 A    5/1998    Yoshikawa et al.
5,863,909 A *  1/1999    Kurita et al. ............... 514/129
6,013,676 A    1/2000    Suzuki et al.

FOREIGN PATENT DOCUMENTS

| JP | 54-080423 A | 6/1979 |
| JP | 55-036458 A | 3/1980 |
| JP | 59-172401 A | 9/1984 |
| JP | 02-040301 A | 2/1990 |
| JP | 07-165515 A | 6/1995 |
| JP | 0 737 682 A1 | 10/1996 |
| JP | 09-235282 A | 9/1997 |
| JP | 2001-151770 A | 6/2001 |
| JP | 2002-308703 A | 10/2002 |
| WO | 97/46092 A1 | 12/1997 |

OTHER PUBLICATIONS

HCAPLUS Abstract 1961:10180(1961).*

* cited by examiner

*Primary Examiner*—John Pak
(74) *Attorney, Agent, or Firm*—Buchanan Ingersoll & Ingersoll PC

(57) ABSTRACT

The present invention provides an aqueous suspension formulation containing (RS)-N-[2-(1,3-dimethylbutyl)thiophene-3-yl]-1-methyl-3-trifluoromethyl-1H-pyrazole-4-carboxamide and having high rain resistance and stable residual effectiveness.

A aqueous suspension formulation for foliar application fungicide of the present invention contains a fungicidal active ingredient, (RS)-N-[2-(1,3-dimethylbutyl)thiophene-3-yl]-1-methyl-3-trifluoromethyl-1H-pyrazole-4-carboxamide, and a polyoxyalkylene rosin acid ester or liquid paraffin, and has improved rain resistance on plant leaves and excellent residual effectiveness.

2 Claims, No Drawings

AQUEOUS SUSPENSION FORMULATION FOR FOLIAR APPLICATION FUNGICIDE

This application is a 371 of PCT/JP04/09986, filed on Jul. 7, 2004.

TECHNICAL FIELD

The present invention relates to an aqueous suspension formulation for foliar application fungicide containing a fungicidal active ingredient, (RS)-N-[2-(1,3-dimethylbutyl)thiophene-3-yl]-1-methyl-3-trifluoromethyl-1H-pyrazole-4-carboxamide, and a polyoxyalkylene resin acid ester or liquid paraffin, and having improved rain resistance.

BACKGROUND ART

In recent years, aqueous suspension formulations referred to as "flowable" have been becoming mainstream of agrichemical formulations for foliar application. A main reason for this is that aqueous suspension formulations cause no generation of dust and thus cause little worker exposure to dust, while formulations such as wettable powders and dust formulations easily cause worker exposure to dust.

On the other hand, the persistence of the effect of a fungicidal active ingredient often decreases during the period of foliar application. Possible causes for this include dilution of the active ingredient on phylloplane with the growth of plants, photodecomposition on the phylloplane, and wash-off of the fungicidal active ingredient from the phylloplane due to rainfall. A non-systemic fungicide easily undergoes a decrease in residual effectiveness due to rainfall because the applied active compound remains on the phylloplane without penetrating and transferring into a plant. In order to maintain a predetermined fungicidal effect, therefore, an excess of agrichemical is applied to impose much labor and economical load on a worker, thereby causing environmental contamination.

It is known that a fungicidal active ingredient, (RS)-N-[2-(1,3-dimethylbutyl)thiophene-3-yl]-1-methyl-3-trifluoromethyl-1H-pyrazole-4-carboxamide, used in the present invention exhibits an excellent effect on a wide variety of diseases (European Unexamined Patent Application publication No. 0737682).

This active compound is water-insoluble and has a high melting point, and an aqueous suspension formulation has been studied for using the compound for foliar application. However, there is known only an aqueous suspension formulation produced by wet-grinding the compound in water simply using a surfactant according to a general formula. In application of a liquid medicine containing the compound involved in the present invention to crops, the persistency of the effect significantly decreased by rainfall thereafter.

In recent, various means for preventing a decrease in the agrichemical effect due to rainfall have been studied. For example, Japanese Unexamined Patent Application Publication No. S54-80423 discloses agrichemical coating agents containing α-starch and thus having high rain resistance. Japanese Unexamined Patent Application Publication No. S59-172401 discloses wettable powders containing a powdery resin added for improving rain resistance. Japanese Unexamined Patent Application Publication No. H02-40301 discloses water-dispersible granules containing polyvinyl alcohol or carboxymethyl cellulose added for improving rain resistance by enhancing sticking tendency. Patent Application WO97/46092 discloses emulsions, aqueous suspo emulsions, wettable powders, suspensions, and water-dispersible granules each containing sorbitan trioleate added for improving rain resistance.

However, when any one of the materials described in the above-described documents or a commercially available general spreading agent functioning as an adjuvant was used for the fungicidal active ingredient of the present invention, no material was found for preventing (improving rain resistance) a decrease in the persistence of the effect of the compound due to rainfall.

[Patent Document 1] Japanese Unexamined Patent Application Publication No. S54-80423
[Patent Document 2] Japanese Unexamined Patent Application Publication No. S59-172401
[Patent Document 3] Japanese Unexamined Patent Application Publication No. H02-40301
[Patent Document 4] Patent Application WO97/46092
[Patent Document 5] European Unexamined Patent Application publication No. 0737682

DISCLOSURE OF INVENTION

An object of the present invention is to provide an aqueous suspension formulation containing a fungicidal active ingredient, (RS)-N-[2-(1,3-dimethylbutyl)thiophene-3-yl]-1-methyl-3-trifluoromethyl-1H-pyrazole-4-carboxamide, having improved adhesion of the active ingredient on phylloplane in foliar application, and thus having improved persistence of the effect of the active ingredient.

As a result of study for solving the above-described problem, the inventors surprisingly found that among conventional known spreading agents, only a polyoxyalkylene resin acid ester or liquid paraffin can improve the rain resistance of the agrichemical active ingredient involved in the present invention, leading to the achievement of the present invention.

Namely, an aqueous suspension formulation for foliar application fungicide of the present invention comprises a fungicidal active ingredient, (RS)-N-[2-(1,3-dimethylbutyl)thiophene-3-yl]-1-methyl-3-trifluoromethyl-1H-pyrazole-4-carboxamide, and a polyoxyalkylene resin acid ester or liquid paraffin.

The present invention can provide an aqueous suspension formulation having improved rain resistance of the active ingredient, (RS)-N-[2-(1,3-dimethylbutyl)thiophene-3-yl]-1-methyl-3-trifluoromethyl-1H-pyrazole-4-carboxamide, on phylloplane in foliar application, and thus having excellent residual effectiveness.

BEST MODE FOR CARRYING OUT THE INVENTION

The present invention relates to an aqueous suspension formulation for foliar application fungicide comprising a fungicidal active ingredient, and a polyoxyalkylene resin acid ester or liquid paraffin added for improving rain resistance.

The fungicidal active ingredient, (RS)-N-[2-(1,3-dimethylbutyl)thiophene-3-yl]-1-methyl-3-trifluoromethyl-1H-pyrazole-4-carboxamide, used in the present invention is an effective compound for a variety of diseases such as grape powdery mildew (*Uncinula necator*), apple powdery mildew (*Podosphaera leucotricha*), apple scab (*Venturia inaequalis*), apple alternaria blotch (*Alternaria mali*), apple rust (*Gymnosporangium yamadae*), apple blossom blight (*Aclerotinia mali*), pear black spot (*Alternaria kikuchiana*), pear scab (*Venturia nashicola*), pear rust (*Gymnosporangium haraeanum), peach brown rot (*Sclerotinia cinerea*), peach scab (*Cladosporium carpophilum*), cucurbits powdery mildew (*Sphaerotheca fuliginea*), tomato leaf mold (*Cladosporium fulvam*), eggplant powdery mildew (*Erysiphe cichoracoarum*), grey mold (*Botrytis cinerea*) and sclerotinia rot or stem rot (*Sclerotinia sclerotiorum*) on vegetables such as cucumbers, tomatoes, strawberries, and grapes.

In the present invention, an auxiliary agent for imparting the rain resistance to the fungicidal ingredient is the polyoxyalkylene resin acid ester or the liquid paraffin.

The polyoxyalkylene resin acid ester is produced by adding an alkylene oxide to a resin acid. Specific examples of the polyoxyalkylene resin acid ester include polyoxyethylene resin acid esters obtained by adding ethylene oxide to resin acids, polyoxypropylene resin acid esters obtained by adding propylene oxide to resin acids, and polyoxyethylene polyoxypropylene resin acid esters obtained by adding ethylene oxides and propylene oxide to resin acids. Polyoxyalkylene rosin acid esters are produced by adding alkylene oxides to rosin acid in resin acids. Examples of the polyoxyalkylene rosin acid esters include polyoxyethylene rosin acid ester obtained by adding ethylene oxide to resin acids, polyoxypropylene rosin acid ester obtained by adding propylene oxide to resin acids, and polyoxyethylene polyoxypropylene rosin acid ester obtained by adding ethylene oxide and propylene oxide to resin acids. The rosin acid is monocarboxylic acid-type diterpene acid distributed in pinus plants and containing abietic acid and pimaric acid as main ingredients. The polyoxyalkylene rosin acid esters are industrially available, and for example, DRA (produced by TOHO Chemical Industry Co., LTd.) series is available.

In order to improve the rain resistance of the fungicidal ingredient according to the present invention, polyoxyethylene resin acid esters and polyoxyethylene-polyoxypropylene resin acid esters among the polyoxyalkylene resin acid esters are preferred, and polyoxyethylene rosin acid ester and polyoxyethylene-polyoxypropylene rosin acid ester are more preferred.

In the present invention, among the polyoxyethylene resin acid esters, a polyoxy resin acid ester produced by adding 1 to 12 mol of ethylene oxide per mol of resin acid is preferred for improving the rain resistance of the fungicidal ingredient, and a polyoxyethylene rosin acid ester produced by adding 1 to 12 mol of ethylene oxide per mol of rosin acid is more preferred.

Among the polyoxyethylene-polyoxypropylene resin acid esters and the polyoxyethylene-polyoxypropylene rosin acid ester, polyoxyethylene-polyoxypropylene resin acid esters and polyoxyethylene-polyoxypropylene rosin acid esters each having a HLB (Hydrophile-Lipophile Balance) of 2 to 13 are preferred for improving the rain resistance of the fungicidal ingredient of the present invention, and a polyoxyethylene-polyoxypropylene rosin acid ester having a HLB of 5 to 11 is particularly preferred.

In the present invention, HLB is generally used as a numerical value which indicates hydrophilicity-hydrophobicity balance of a surfactant. A surfactant becomes water-insoluble by being lipophiic when a HLB value is low, while a surfactant becomes water-insoluble by being hydrophilic when a HLB value is high. The value of HLB used in the present invention is calculated by the following equation (1):

$$HLB=(\text{molecular weight of hydrophilic group part}/\text{total molecular weight})\times(100/5) \quad \text{Equation 1}$$

In this equation, the molecular weight of a hydrophilic group part corresponds to the molecular weight of the ethylene oxide added.

In order to achieve the effect of improving the rain resistance of the fungicidal ingredient of the present invention, the mixing amount of the polyoxyalkylene resin acid ester is generally in the range of 1 to 70 parts by weight regardless of the type of the alkylene group. In particular, in the use of the polyoxyethylene rosin acid ester or polyoxyethylene polyoxypropylene rosin acid ester, an adequate mixing amount is in the range of 10 to 50 parts by weight. With a mixing amount less than this range, the effect is unstable, while with a mixing amount of over this range, the viscosity of the suspension increases and as a consequence, the physical properties of the suspension tends to degrade.

The liquid paraffin exhibiting the same effect as that of the polyoxyalkylene resin acid esters contains alkylnaphthenic hydrocarbons as a main component, belongs to lubricants in view of the boiling point, and comprises a mixture of liquid saturated hydrocarbons with very high purity. The liquid paraffin is different from materials generally referred to as "normal paraffin" and "isoparaffin".

In order to achieve the effect of improving the rain resistance of the fungicidal ingredient of the present invention, the mixing amount of liquid paraffin in the formulation is generally in the range of 1 to 80 parts by weight, and preferably in the range of 20 to 60 parts by weight.

Examples usable as the liquid paraffin include CRYSTOL N52, CRYSTOL N72, CRYSTOL N82, CRYSTOL N122, CRYSTOL N172, CRYSTOL N262, CRYSTOL N352, and CRYSTOL 542 (produced by Exxon Mobile Co., Ltd.);

COSMO WHITE P60, COSMO WHITE P70, COSMO WHITE P120, COSMO WHITE P200, COSMO WHITE P260, and COSMO WHITE 350 (produced by Cosmo Oil Lubricants Co., Ltd.);

Dufny Oil KP8, Dufny Oil KP15, Dufny Oil KP32, Dufny Oil KP68, Dufny Oil KP100, Dufny Oil CP12N, Dufny Oil CP15N, and Dufny Oil CP32N (produced by Idemitsu Kosan Co., Ltd.);and MORESCO WHITE P60, MORESCO WHITE P100, MORESCO WHITE P120, MORESCO WHITE P230, and MORESCO WHITE P350P (produced by Matsumura Oil Research Corp.). However, the liquid paraffin is not limited to these examples.

The present invention provides for an aqueous suspension formulation for foliar fungicide and method for improving resistance to rain comprising mixing (RS)-N-[2-(1,3-dimethylbutyl)thiophene-3-yl]-1-methyl-3-trifluoromethyl-1 H-pyrazole-4-carboxamide, and 10-50 parts by weight of a polyoxyalkylene resin acid ester or 20 to 60 parts by weight of a liquid paraffin, based on 100 parts by weight of the aqueous suspension formulation, wherein the liquid paraffin contains alkylnaphthenic hydrocarbons as a main component and saturated hydrocarbons, and wherein the polyoxyalkylene resin acid ester is a polyoxyethylene rosin acid ester which has the average number of moles of ethylene oxide added to the polyoxyethylene rosin acid ester of 1 to 12 per mole of rosin acid, or a polyoxyethylene polyoxypropylene rosin acid ester which has a HLB of 2 to 13 calculated according to the following equation:

$$HLB=(\text{molecular weight of hydrophilic part}/\text{total molecular weight})\times(100/5).$$

The aqueous suspension formulation of the present invention can be produced by the following two methods:

A first method of production comprises mixing the fungicidal ingredient of the present invention, the polyoxyalkylene resin acid ester or liquid paraffin, a surfactant, and ion-exchanged water, and if required, a defoaming agent and an antifreezing agent, wet-grinding the resultant mixture to a desired particle diameter, and then mixing the prepared mixture with a thickener aqueous solution containing an antiseptic mildewproofing agent.

A second method of production comprises mixing the fungicidal active ingredient, a surfactant, and ion-exchanged water, and if required, a defoaming agent and an antifreezing agent, wet-grinding the resultant mixture to a desired particle diameter, and then further mixing the prepared mixture with an emulsion separately prepared from the polyoxyalkylene resin acid ester or liquid paraffin, a surfactant, and ion-exchanged water, and a thickener aqueous solution containing an antiseptic mildewproofing agent. In this method, the emulsion of the polyoxyalkylene resin acid ester or liquid paraffin may be prepared by a known method such as a phase inversion emulsification method or a mechanical emulsification method.

Examples usable as the surfactant for the aqueous suspension formulation of the present invention include nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene castor oil, polyoxyethylene alkyl ethers, polyoxyethylene alkyl phenyl esters, polyoxyethylene dialkyl phenyl ethers, formalin condensates of polyoxyethylene alkyl phenyl ethers, polyoxyethylene-polyoxypropylene block polymers, alkyl polyoxyethylene-polyoxypropylene block polymer ethers, alkyl phenyl polyoxyethylene-polyoxypropylene block polymer ethers, polyoxyethylene alkylamines, polyoxyethylene fatty acid amides, polyoxyethylene bisphenyl ethers, polyoxyalkylene benzyl phenyl ethers, polyoxyalkylene styryl phenyl ethers, and higher-alcohol polyoxyalkylene adduct- or polyoxyethylene ether- or ester-type silicon or fluorine surfactants composed of;

anionic surfactants such as alkyl sulfates, polyoxyethylene alkyl ether sulfates, polyoxyethylene alkyl phenyl ether sulfates, polyoxyethylene benzyl phenyl ether sulfates, polyoxyethylene styryl phenyl ether sulfates, polyoxyethylene polyoxypropylene block polymer sulfates, paraffin sulfonates, alkane sulfonates, AOS, dialkyl sulfosuccinates, alkylbenzene sulfonates, naphthalene sulfonates, dialkyl naphthalene sulfonates, formalin condensates of naphthalene sulfonates, alkyl diphenyl ether disulfonates, lignin sulfonates, polyoxyethylene alkyl phenyl ether sulfonates, polyoxyethylene alkyl ether sulfosuccinic acid half esters, fatty acid salts, N-methyl-fatty acid sarcosinates, resin acid salts, polyoxyethylene alkyl ether phosphates polyoxyethylene phenyl ether phosphates, polyoxyethylene dialkyl phenyl ether phosphates, polyoxyethylene benzylphenyl ether phosphates, polyoxyethylene benzylphenyl phenyl ether phosphates, polyoxyethylene styrylphenyl ether phosphates, polyoxyethylene styrylphenyl phenyl ether phosphates, polyoxyethylene polyoxypropylene block polymer phosphates, phosphatidylcholine, phosphatidyl ethanol imine, and alkyl phosphates;

polyanionic polymer surfactants derived from acrylic acid, acrylonitrile, and acrylamidomethyl propanesulfonic acid;

cationic surfactants such as alkyltrimethylammonium chloride, methyl polyoxyethylene alkylammonium chloride, alkyl N-methylpyridinium bromide, monomethylammonium chloride, dialkylmethylammonium chloride, alkylpentamethylpropyleneamine dichloride, alkyldimethylbenzalkonium chloride, and benzethonium chloride; and ampholytic surfactants such as dialkyldiaminoethyl betain and alkyldimethylbenzyl betain. However, the surfactant is not limited to these examples.

Also, the antiseptic mildewproofing agent such as 1,2-benzoisothiazoline-3-one, the defoaming agent such as a silicone compound, the thickener such as xanthane gum, and the antifreezing agent such as propylene glycol may be added as occasion demands.

Although the present invention will be described in further detail below with reference to examples, the present invention is not limited to these examples.

COMPARATIVE EXAMPLE

Five parts by weight of (RS)-N-[2-(1,3-dimethylbutyl)thiophene-3-yl]-1-methyl-3-trifluoromethyl-1H-pyrazole-4-carboxamide (referred to as a "fungicidal active ingredient" hereinafter), 5 parts by weight of sodium salt of naphthalenesulfonic acid formaldehyde condensate, 1 part by weight of polyoxyethylene aryl phenyl ether, 5 parts by weight of propylene glycol, 0.1 part by weight of a silicon-based defoaming agent, 0.2 part by weight of xanthane gum, and 83.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare a fungicidal aqueous suspension formulation.

COMPARATIVE EXAMPLE 2

Five parts by weight of the fungicidal active ingredient, 40 parts by weight of a polyoxyethylene rosin acid ester (number of moles of ethylene oxide added, 15), 5 parts by weight of sodium salt of naphthalenesulfonic acid formaldehyde condensate, 1 part by weight of polyoxyethylene aryl phenyl ether, 5 parts by weight of propylene glycol, 0.1 part by weight of a silicon-based defoaming agent, 0.2 part by weight of xanthane gum, and 43.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare a fungicidal aqueous suspension formulation.

COMPARATIVE EXAMPLE 3

Five parts by weight of the fungicidal active ingredient, 1 part by weight of a polyoxyethylene aryl phenyl ether, 0.1 part by weight of a silicon-based defoaming agent, and 13.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare an aqueous suspension. The resultant aqueous suspension was mixed with an emulsion to prepare a fungicidal aqueous suspension formulation. The emulsion was prepared by mechanically emulsifying 40 parts by weight of normal paraffin, 2 parts by weight of a polyanionic polymer surfactant (produced by Kao Corporation), and 38.2 parts by weight of ion-exchanged water with homo-mixer Mark-II (produced by Tokushu Kika Kogyo Co., Ltd.).

COMPARATIVE EXAMPLE 4

Five parts by weight of the fungicidal active ingredient, 1 part by weight of a polyoxyethylene aryl phenyl ether, 0.1 part by weight of a silicon-based defoaming agent, and 13.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare an aqueous suspension. The resultant aqueous suspension was mixed with an emulsion to prepare a fungicidal aqueous suspension formulation. The emulsion was prepared by mechanically emulsifying 40 parts by weight of isoparaffin, 2 parts by weight of a polyanionic polymer surfactant (produced by Kao Corporation), and 38.2 parts by weight of ion-exchanged water with homo-mixer Mark-II (produced by Tokushu Kika Kogyo Co., Ltd.).

EXAMPLE 1

Five parts by weight of the fungicidal active ingredient, 40 parts by weight of a polyoxyethylene rosin acid ester (number of moles of ethylene oxide added, 12), 5 parts by weight of sodium salt of naphthalenesulfonic acid formaldehyde condensate, 1 part by weight of polyoxyethylene aryl phenyl ether, 5 parts by weight of propylene glycol, 0.1 part by weight of a silicon-based defoaming agent, 0.2 part by weight of xanthane gum, and 43.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare a fungicidal aqueous suspension formulation.

EXAMPLE 2

The same operation as that in Example 1 was performed to prepare a fungicidal aqueous suspension except that 40 parts by weight of a polyoxyethylene rosin acid ester (number of moles of ethylene oxide added: 6) was used.

EXAMPLE 3

Five parts by weight of the fungicidal active ingredient, 1 part by weight of a polyoxyethylene aryl phenyl ether, 0.2 part by weight of xanthane gum, 0.1 part by weight of a silicon-based defoaming agent, and 33.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare an aqueous suspension. The resultant aqueous suspension was mixed with an emulsion to prepare a fungicidal aqueous suspension formulation. The emulsion was prepared by phase inversion emulsification of 40 parts by weight of a polyoxyethylene rosin acid ester (number of moles of ethylene oxide added: 3), 2 parts by weight of polyoxyethylene aryl phenyl ether sulfate, 2 parts by weight of polyoxyallyl ether polymer, and 16 parts by weight of ion-exchanged water.

EXAMPLE 4

The same operation as that in Example 3 was performed to prepare a fungicidal aqueous suspension formulation except that 15 parts by weight of a polyoxyethylene rosin acid ester (number of moles of ethylene oxide added: 3) was used.

EXAMPLE 5

Five parts by weight of the fungicidal active ingredient, 40 parts by weight of a polyoxyethylene polyoxypropylene rosin acid ester (number of moles of ethylene oxide added, 12; number of moles of propylene oxide added, 6)(HLB 9.1), 5 parts by weight of sodium salt of naphthalenesulfonic acid formaldehyde condensate, 1 part by weight of polyoxyethylene aryl phenyl ether, 5 parts by weight of propylene glycol, 0.1 part by weight of a silicon-based defoaming agent, 0.2 part by weight of xanthane gum, and 43.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare a fungicidal aqueous suspension formulation.

EXAMPLE 6

Five parts by weight of the fungicidal active ingredient, 1 part by weight of a polyoxyethylene aryl phenyl ether, 0.2 parts by weight of xanthane gum, 0.1 part by weight of a silicon-based defoaming agent, and 33.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare an aqueous suspension. The resultant aqueous suspension was mixed with an emulsion to prepare a fungicidal aqueous suspension formulation. The emulsion was prepared by phase inversion emulsification of 40 parts by weight of a polyoxyethylene polyoxypropylene rosin acid ester (number of moles of ethylene oxide added, 12; number of moles of propylene oxide added, 12)(HLB 7.0), 2 parts by weight of polyoxyethylene aryl phenyl ether sulfate, 2 parts by weight of polyoxyallyl ether polymer, and 16 parts by weight of ion-exchanged water.

EXAMPLE 7

The same operation as that in Example 6 was preformed to prepare a fungicidal aqueous suspension formulation except that 40 parts by weight of a polyoxyethylene polyoxypropylene rosin acid ester (number of moles of ethylene oxide added, 3; number of moles of propylene oxide added, 3)(HLB 4.5) was used.

EXAMPLE 8

Five parts by weight of the fungicidal active ingredient, 1 part by weight of a polyoxyethylene aryl phenyl ether, 0.1 part by weight of a silicon-based defoaming agent, and 13.7 parts by weight of ion-exchanged water were mixed to form a slurry. Then, the resultant slurry was wet-ground by Dyno Mill KDL (produced by Shinmaru Enterprise Co.,) using glass beads of 0.75 mm in diameter to prepare an aqueous suspension. The resultant aqueous suspension was mixed with an emulsion to prepare a fungicidal aqueous suspension formulation. The emulsion was prepared by mechanically emulsifying 40 parts by weight of liquid paraffin (trade name COSMO WHITE P70 (produced by Cosmo Oil Lubricants Co., Ltd.)), 2 parts by weight of a polyanionic polymer surfactant (produced by Kao Corporation), and 38.2 parts by weight of ion-exchanged water with homo-mixer Mark-II (produced by Tokushu Kika Kogyo Co., Ltd.).

EXAMPLE 9

The same operation as that in Example 1 was performed to prepare a fungicidal aqueous suspension except that 20 parts by weight of liquid paraffin (trade name COSMO WHITE P70 (produced by Cosmo Oil Lubricants Co., Ltd.)) was used.

EXAMPLE 10

The same operation as that in Example 1 was performed to prepare a fungicidal aqueous suspension except that 40 parts by weight of liquid paraffin (trade name MORESCO WHITE OIL P230 (produced by Matsumura Oil Research Corp.)) was used.

TEST EXAMPLE 1

Evaluation of Rain Resistance

The fungicidal aqueous suspension formulation prepared in each of Comparative Examples 1 to 4 and Examples 1 to 10 was diluted with tap water so that the concentration of the fungicidal active ingredient was 100 ppm. Then, foliar application was performed in such a manner that 40 ml of the diluted solution per one pot planted two bean plants (cotyledon stage) in each of two pots, after cotyledon leaves of bean plants were spreaded. One day after, 20 ml of rain was applied for 20 minutes from an artificial rainfall apparatus. After drying in air, six cotyledon leaves were cut off, and the surface area of each leaf was measured by AREA METER mk2 (produced by DELTA-T DEVICES LTD). Then, the leaves were immersed in 75% methanol for 1 minute to extract the chemical, and the extract was filtered with gauze and a syringe filter of 0.45 μm to prepare a sample. The deposit of the fungicidal active ingredient on the leaves was measured by high-performance liquid chromatographic analysis under the conditions below, and the residual ratio was calculated according to the calculation equation (2) below. The results are shown in Table 1.

Residual ratio=(deposit of fungicidal active ingredient after rainfall/deposit of fungicidal active ingredient before rainfall)×100    Equation 2

Conditions of HPLC
 Mobile phase; methanol:water=75:25(v/v)
 Wavelength; 250 nm
 Flow rate; 1.0 ml/min.
 Column; Waters Symmetryshild RP 8.5μ, diameter 4.6 mm, length 250 mm
 Pump; LC-6A produced by Shimadzu Corporation
 Detector; SPD-6A produced by Shimadzu Corporation

TABLE 1

| | Mixed material | Numbers of moles of ethylene oxide and propylene oxide added | Mixing amount (Parts by weight) | Residual ratio (%) |
|---|---|---|---|---|
| Comp. Example 1 | — | — | 0 | 20 |
| Comp. Example 2 | Polyoxyethylene rosin acid ester | Ethylene oxide 15 | 40 | 26 |
| Comp. Example 3 | Normal paraffin | — | 30 | 24 |
| Comp. Example 4 | Isoparaffin | — | 30 | 26 |
| Example 1 | Polyoxyethylene rosin acid ester | Ethylene oxide 12 | 40 | 39 |
| Example 2 | Polyoxyethylene rosin acid ester | Ethylene oxide 6 | 40 | 42 |
| Example 3 | Polyoxyethylene rosin acid ester | Ethylene oxide 3 | 40 | 46 |
| Example 4 | Polyoxyethylene rosin acid ester | Ethylene oxide 3 | 15 | 40 |
| Example 5 | Polyoxyethylene polyoxypropylene rosin acid ester | Ethylene oxide 12 Propylene oxide 6 | 40 | 42 |
| Example 6 | Polyoxyethylene polyoxypropylene rosin acid ester | Ethylene oxide 12 Propylene oxide 12 | 40 | 44 |
| Example 7 | Polyoxyethylene polyoxypropylene rosin acid ester | Ethylene oxide 3 Propylene oxide 3 | 40 | 49 |
| Example 8 | Liquid paraffin | — | 40 | 49 |
| Example 9 | Liquid paraffin | — | 20 | 42 |
| Example 10 | Liquid paraffin | — | 40 | 47 |

TEST EXAMPLE 2

Effect on Bean Grey Mold

Two bean plants were planted in one pot having a diameter of 7.5 cm. Eighty milliliters of the aqueous suspension formulation prepared in each of Examples 1, 3, 5, and 8 per four plastic pots was applied to bean cotyledon leaves (kidney bean "Green Top" variety, spreaded cotyledon leaves). One day after, rainfall of 20 mm of rain was applied over 1 hour from an artificial rainfall apparatus. After drying in air, the bean cotyledon leaves were cut off and placed in a closed vessel (ice cup of 9 cm in diameter) containing wetted filter paper. On the other hand, a spore suspension containing $1\times10^6$ ml of spores of grey mold fungi (*Botrytis cinerea*) was prepared, and filter paper of 8 mm in diameter impregnated with the spore suspension was placed on the bean leaves for inoculation. After the leaves were allowed to stand at 20° C. for 4 days in the dark, the diameter of a spot was measured to determine a preventive value according to the equation (Equation 3) below. The results are shown in Table 2.

Preventive value=(spot diameter in untreated region−spot diameter in treated region)/spot diameter in untreated region×100    Equation 3

TABLE 2

| | Concentration (ppm) | Preventive value |
|---|---|---|
| Suspension in Example 1 | 25 | 94 |
| | 50 | 96 |
| | 100 | 99 |
| Suspension in Example 3 | 25 | 78 |
| | 50 | 88 |
| | 100 | 91 |

TABLE 2-continued

|  | Concentration (ppm) | Preventive value |
|---|---|---|
| Suspension in Example 5 | 25 | 92 |
|  | 50 | 98 |
|  | 100 | 98 |
| Suspension in Example 8 | 25 | 84 |
|  | 50 | 94 |
|  | 100 | 99 |
| Suspension in Comparative Example 1 | 25 | 59 |
|  | 50 | 65 |
|  | 100 | 72 |
| Suspension in Comparative Example 2 | 25 | 61 |
|  | 50 | 72 |
|  | 100 | 84 |
| Suspension in Comparative Example 3 | 25 | 50 |
|  | 50 | 70 |
|  | 100 | 89 |

Tables 1 and 2 indicate that in foliar application of the fungicidal suspension of the present invention containing the polyoxyethlene rosin acid ester, polyoxyethylene polyoxyethlene rosin acid ester having a HLB of 2 to 13, or liquid paraffin, the rain resistance is significantly improved, as compared with foliar application of the suspension not containing the polyoxyethylene rosin acid ester, polyoxyethylene polyoxypropylene rosin acid ester having a HLB value of 2 to 13, or liquid paraffin.

The invention claimed is:

1. An aqueous suspension formulation for foliar application fungicide, comprising a fungicidal active ingredient, (RS)-N-[2-(1,3-dimethylbutyl)thiophene-3-yl]-1-methyl-3-trifluoromethyl-1H-pyrazole-4-carboxamide, and 10 to 50 parts by weight of a polyoxyalkylene resin acid ester or 20 to 60 parts by weight of a liquid paraffin, based on 100 parts by weight of the aqueous suspension formulation, wherein the liquid paraffin contains alkylnaphthenic hydrocarbons as a main component and saturated hydrocarbons, and wherein the polyoxyalkylene resin acid ester is a polyoxyethylene rosin acid ester which has the average number of moles of ethylene oxide added to the polyoxyethylene rosin acid ester of 1 to 12 per mole of rosin acid, or a polyoxyethylene polyoxypropylene rosin acid ester which has a HLB of 2 to 13 calculated according to the following equation:

$HLB$=(molecular weight of hydrophilic part/total molecular weight)×(100/5).

2. A method for improving resistance to rain, comprising utilizing an aqueous suspension formulation for foliar application fungicide, the aqueous suspension formulation comprising a fungicidal active ingredient, (RS)-N-[2-(1,3-dimethylbutyl)thiophene-3-yl]-1-methyl-3-trifluoromethyl-1H-pyrazole-4-carboxamide, and 10 to 50 parts by weight of a polyoxyalkylene resin acid ester or 20 to 60 parts by weight of a liquid paraffin, based on 100 parts by weight of the aqueous suspension formulation, wherein the liquid paraffin contains alkylnaphthenic hydrocarbons as a main component and saturated hydrocarbons, and wherein the polyoxyalkylene resin acid ester is a polyoxyethylene rosin acid ester which has the average number of moles of ethylene oxide added to the polyoxyethylene rosin acid ester of 1 to 12 per mole of rosin acid, or a polyoxyethylene polyoxypropylene rosin acid ester which has a HLB of 2 to 13 calculated according to the following equation:

$HLB$=(molecular weight of hydrophilic part/total molecular weight)×(100/5).

* * * * *